(12) United States Patent
Zatirukha

(10) Patent No.: US 12,349,921 B2
(45) Date of Patent: Jul. 8, 2025

(54) STYPTIC HARNESS TOURNIQUET

(71) Applicant: Volodymyr Zatirukha, Dnipro (UA)

(72) Inventor: Volodymyr Zatirukha, Dnipro (UA)

( * ) Notice: Subject to any disclaimer, the term of this patent is extended or adjusted under 35 U.S.C. 154(b) by 0 days.

(21) Appl. No.: 18/878,081

(22) PCT Filed: Jul. 29, 2022

(86) PCT No.: PCT/UA2022/000041
§ 371 (c)(1),
(2) Date: Dec. 23, 2024

(87) PCT Pub. No.: WO2024/010560
PCT Pub. Date: Jan. 11, 2024

(65) Prior Publication Data
US 2025/0169827 A1 May 29, 2025

(30) Foreign Application Priority Data
Jul. 4, 2022 (UA) .............................. u 2022 02299

(51) Int. Cl.
*A61B 17/132* (2006.01)
(52) U.S. Cl.
CPC ................................ *A61B 17/1322* (2013.01)
(58) Field of Classification Search
CPC .............. A61B 17/132; A61B 17/1322; A61B 17/1325
See application file for complete search history.

(56) References Cited

U.S. PATENT DOCUMENTS

| | | | | |
|---|---|---|---|---|
| 7,892,253 B2 * | 2/2011 | Esposito | ............ | A61B 17/1327 606/203 |
| 8,047,850 B2 * | 11/2011 | Esposito | ................ | G09B 23/28 434/262 |
| 8,343,182 B2 * | 1/2013 | Kirkham | ............ | A61B 17/1322 606/203 |
| 8,926,651 B2 * | 1/2015 | McDonald | .............. | G01L 5/047 606/203 |
| 9,855,055 B2 * | 1/2018 | Kosiorek | ............ | A61B 17/1327 |
| D906,168 S * | 12/2020 | Parsons | ........................ | D11/218 |
| 2009/0005804 A1 | 1/2009 | Esposito | | |
| 2010/0057120 A1 | 3/2010 | Kirkham | | |
| 2010/0286724 A1 * | 11/2010 | Rose | .................. | A61B 17/1322 606/203 |

(Continued)

FOREIGN PATENT DOCUMENTS

| | | |
|---|---|---|
| DE | 20201710298 U1 | 6/2017 |
| RU | 205951 U1 | 8/2021 |
| WO | WO2008/060524 A2 | 5/2008 |

*Primary Examiner* — Ryan J. Severson

(57) ABSTRACT

A styptic harness tourniquet used by hands for providing a first aid to stop external arterial bleeding from injured limbs. The harness consists of a casing with Velcro fastener, a sling, a buckle at one end of the casing and a base with fixator with strap, windlass rod attached to the sling. The casing has at least two layers, the buckle contains at least one hole, the base contains at least six holes, and the strap of the fixator contains at least one hole. The holes in the buckle and base have teeth on one side. The windlass rod contains at least 1 cm of a smooth surface and at least 1.5 cm of a ribbed surface at the edges. The harness increases the reliability of the structure and the efficiency of its operation.

5 Claims, 3 Drawing Sheets

(56) References Cited

U.S. PATENT DOCUMENTS

| | | | |
|---|---|---|---|
| 2012/0071917 A1* | 3/2012 | McDonald | G01L 5/102 |
| | | | 116/212 |
| 2015/0094756 A1 | 4/2015 | Kosiorek | |
| 2018/0193033 A1* | 7/2018 | Kosiorek | A61B 17/1322 |
| 2021/0259395 A1 | 8/2021 | Larson | |

* cited by examiner

STYPTIC HARNESS TOURNIQUET

RELATED APPLICATIONS

This application is a National Phase of PCT Patent Application No. PCT/UA2022/000041 having International filing date of 29 Jul. 2022, which claims the benefit of priority Ukrainina patent application number u202202299 filed on Jul. 4, 2022.

TECHNICAL FIELD

The invention applies to medical field, primarily as medical equipment, as styptic harness tourniquet that is applied with one or two hands, and can be used in providing first aid to stop external arterial bleeding from injured limbs.

BACKGROUND ART

Esmarch's rubber hemostatic tourniquets are known. The disadvantage of such tourniquets is the inability to control compression, as a result of which pain occurs 10 when tightening it. In addition, such tourniquet can't be applied with one hand and need to be loosened and tightened again.

A known hemostatic tourniquet containing an elastic ribbon with a fringe effect on one side, a device for forming a knot with the fringe inward and a device for fixing 15 the applied tourniquet, the device for forming a knot is made in the form of a buckle of a rectangular shape, and a device for fixing the applied tourniquet is fixed on the free end of the braid there is a device for fixing of applied tourniquet, that consisting of at least 2.5 turns (RF Patent No. 76791, IPC A61B17/12, publ. 10 Oct. 2008).

The disadvantage of the known hemostatic tourniquet is the high probability of excessive compression of the injured limb and pinching of the skin of the injured limb. In addition, the disadvantage of the known tourniquet is insufficient reliability and duration of fixation of the free end of the strap after applying the tourniquet.

A known hemostatic tourniquet containing a non-extensible ribbon, an extensible ribbon in the form of a rubber element connected to two steel rectangular rings on two sides, with rectangles and the inscriptions "Thigh", "Shoulder" applied to it, and a windlass rod, at the same time non-extensible the tape forms a double loop 30 when the tourniquet is applied, and the windlass rod is made with a hole in the middle and cone-shaped arrow-shaped ends (RF Patent No. 76791, IPC A61B17/12, publ. 10 Oct. 2008).

The disadvantage of the known hemostatic tourniquet is the high probability of excessive compression of the injured limb and pinching of the skin of the injured limb. In addition, the disadvantage of the known tourniquet is the lack of reliability of fixing the windlass rod after applying the harness with the possibility of injury to the limb when the strap is punctured by the windlass rod.

A hemostatic tourniquet is known, which contains a strap, at one end of which a buckle is fixed, and at the other end a tip is made, slings that are located in the 10 inner cavity of the strap and having fixed ends, and a node for tightening and fixing the applied tourniquet, while the knot tightening and fixing of the applied tourniquet is installed in the center of the strap and contains a base on which the tourniquet application time indicator is fixed and a coil with the possibility of rotation are located, in the central hole of which a lever is fixed, on the side surface of the coil on both sides of the lever, central radial axis notches are made and disc-shaped side guides, in addition, on both edges of the base in front of the coil and behind it, radially oriented notches are made, while the straps are successively pulled through the notches in front of the coil, the notch in the radial axis of the coil, and the notch after the coil (RF U.S. Pat. No. 2,531,449, IPC A61B17/12, publ.20 Oct. 2014).

The disadvantage of the known hemostatic tourniquet is the complexity of performing the tightening and fixing of the tourniquet, which complicates the process of applying and tightening the tourniquet, resulting in the possibility of excessive compression of the injured limb and pinching of the skin of the injured limb. In addition, the disadvantage of the known harness is insufficient reliability and duration of fixation of the free end of the strap after applying the tourniquet.

A hemostatic tourniquet is known, which contains a strap, at one end of which a buckle is fixed, and at the other end a tip is made, a sling, which is located in the inner cavity of the strap and has fixed ends, and a knot for tightening and fixing the applied tourniquet; the strap is formed by the initial part, inside which two inserts are fixed overlapping with the possibility of moving one along the other, and the long part, on which a textile Velcro® fastener is additionally fixed on the front side, made in the form of a ribbon, on which loop and hook sections are diagonally located alternately, or in the form of a ribbon, where the loops and hooks are mixed located, and the knot for tightening and fixing the tourniquet clamp consists of a windlass rod with a hole and a windlass rod fixator, which are fixed on the front side of the initial part of the strap, while on the front side of the initial part of the strap has two holes with a frame for holding a windlass rod located above them, which connects the adjacent ends of the sections formed by the slots of the 10 initial part of the strap, a windlass rod is placed above the frame for holding the windlass rod, and through the specified two holes through the windlass rod fixator is brought out and extended in the hole of the windlass rod with the possibility of twisting it to tighten the strap, followed by fixing one of the ends of the windlass rod in the windlass rod fixator; the fixator of windlass rod has a triangular shape and contains two protrusions to limit the movement of the turnaround rod; the fixator of windlass rod is fixed on the surface of the initial part of the strap with the help of a short strap; the frame the fixator of windlass rod has a rectangular shape; insets in the initial part of the strap have a rectangular shape and are made of plastic; on one of the ends of the strap, a ribbon is additionally fixed, made with the 20 possibility of applying an inscription with sharp objects; additionally contains a textile fastener made in the form of Velcro® fastener with the possibility of fixing the windlass rod and the free end of the strap after applying the tourniquet; Velcro® fastener is made with the possibility of writing on it with sharp objects or a marker; the tip of the strap is additionally equipped with a plastic insert; the buckle is made in the form of a metal double rectangular frame with a lintel, which has teeth for fixing the tourniquet; the strap is made with a width of 4 cm and a length of 93 cm; the sling is made with a width of 2 to 2.5 cm; the sling is made of textile fabrics; Velcro® fastener and strap are made of textile or polyamide fabrics;

the windlass rod and the windlass rod fixator are made of duralumin or steel (UA U.S. Pat. No. 103,336, IPC A61B 17/12, publ. 10 Dec. 2015, Bull. No. 23).

The disadvantages of the known hemostatic tourniquet are low reliability and efficiency of operation.

Prior art to the claimed styptic harness tourniquet is a combat application tourniquet, containing a casing with a Velcro® fastener, in which there is an inner band (hereinafter referred to as a sling) with a plastic windlass rod (hereinafter referred to as a windlass rod); at the end of the casing there is a plastic one-way buckle (hereafter buckle) with one hole and a stabilization plate (hereafter base) with four holes, with a windlass clip (hereafter fixator) and a windlass strap (hereafter strap of the fixator) (Access mode: www.combattourniquet.com).

The disadvantages of this combat application tourniquet are the low reliability of the design and the low efficiency of its operation due to the thin and soft casing and when used (twisting the windlass rod) causes painful feeling when applying, the lower strap of the casing is located on the surface of the base, which in some cases can lead to winding under the windlass rod together with the casing of the lower strap of the casing and self-blocking, which leads to incomplete coverage of the blood flow, the casing with Velcro® is too soft, which does not give a stable loop when applying and can interfere with self-help.

RU 205 951 U1 discloses a tourniquet having a casing, a buckle, a base, and a windlass rod. DE 20 2017 102981 U1, US 2021/259395 A1, WO 2008/060524 A2, US 2010/057120 A1, US 2009/005804 A1, and US 2015/094756 A1 disclose further tourniquets.

THE INVENTION

The object of the invention is to create such a styptic harness tourniquet, in which, due to structural changes, it is possible to increase the reliability of the structure, increase the efficiency of its operation, and reduce pain during application. The object is achieved by the fact that styptic harness tourniquet, which consists of a casing with Velcro® fastener, in which a sling is located; at one end of the casing 30 there is a buckle and a base on which the fixator and the strap of the fixator are located; a windlass rod is attached to the sling, which is characterized that the casing has at least two layers, the buckle contains at least one hole, the base contains at least six holes, strap of the fixator contains at least one hole; holes of the buckle and base have teeth on at least one side;
   plastic is used as the material of the base and fixator;
   Aluminum, aluminum alloys, and plastic are used as materials for windlass rod and buckle;
   the teeth of the holes can have a rectangular, rounded, trapezoidal, square shape;
   the windlass rod contains at least 1 cm of a smooth surface and at least 1.5 cm 10 of a ribbed surface at the edges.

Figures 1, 2:
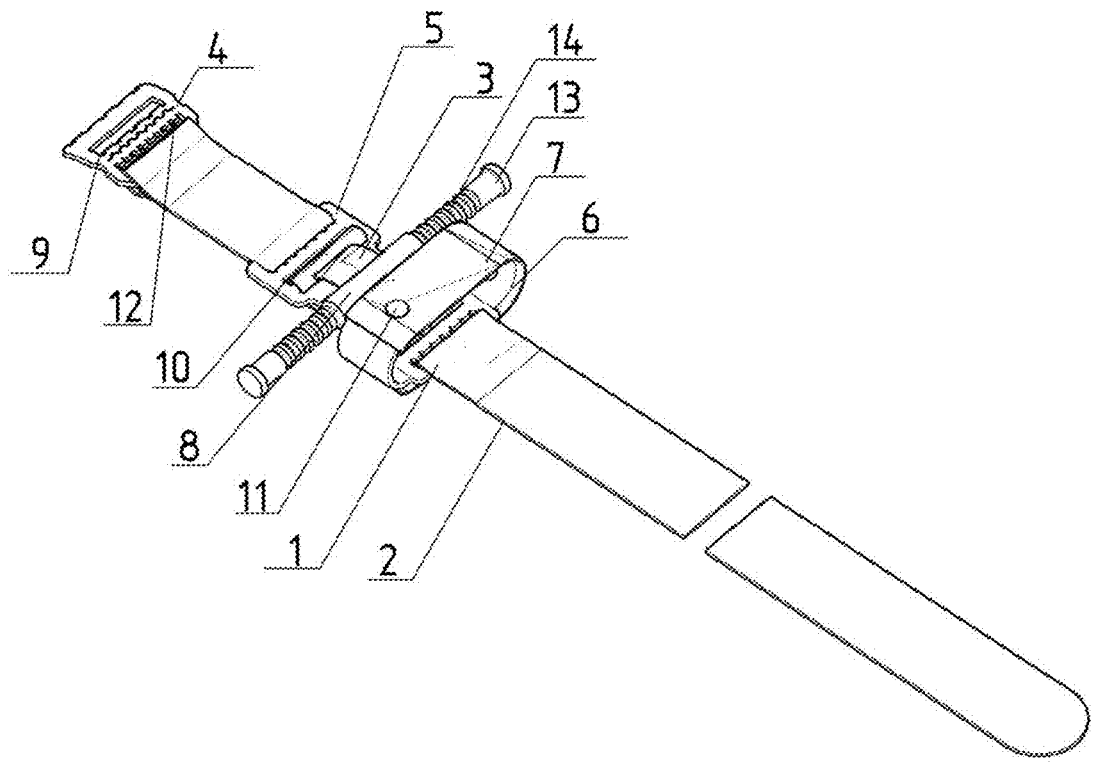
FIG. 1 depicts the general view of the styptic harness tourniquet.
FIG. 2 depicts the general view of the buckle.
Figure 3:
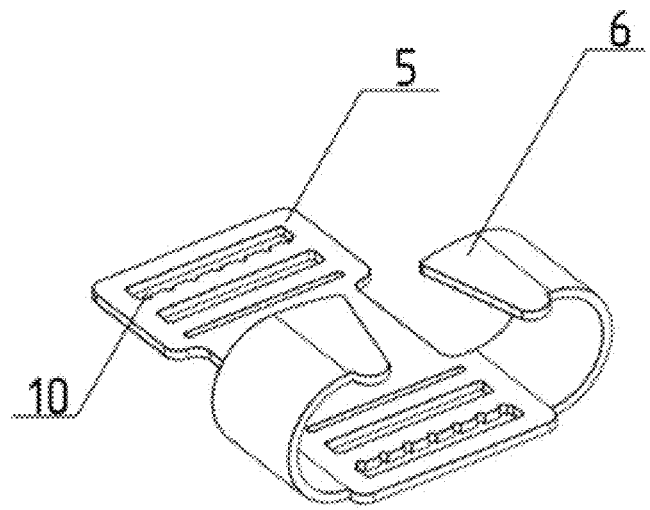
FIG. 3 depicts the general view of the base.
Figure 4:
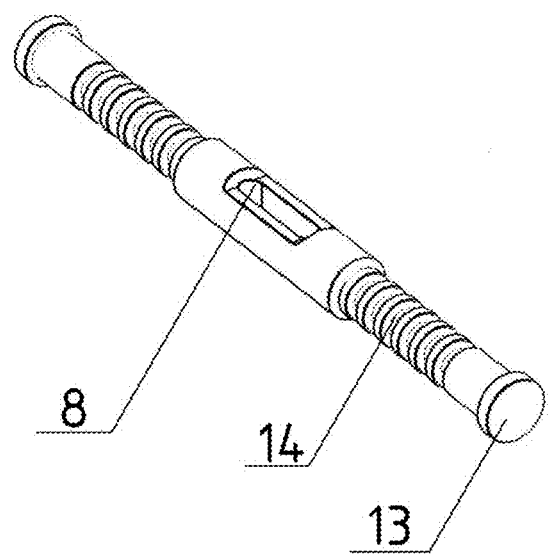
FIG. 4 depicts the general view of the windlass rod.
Figure 5:
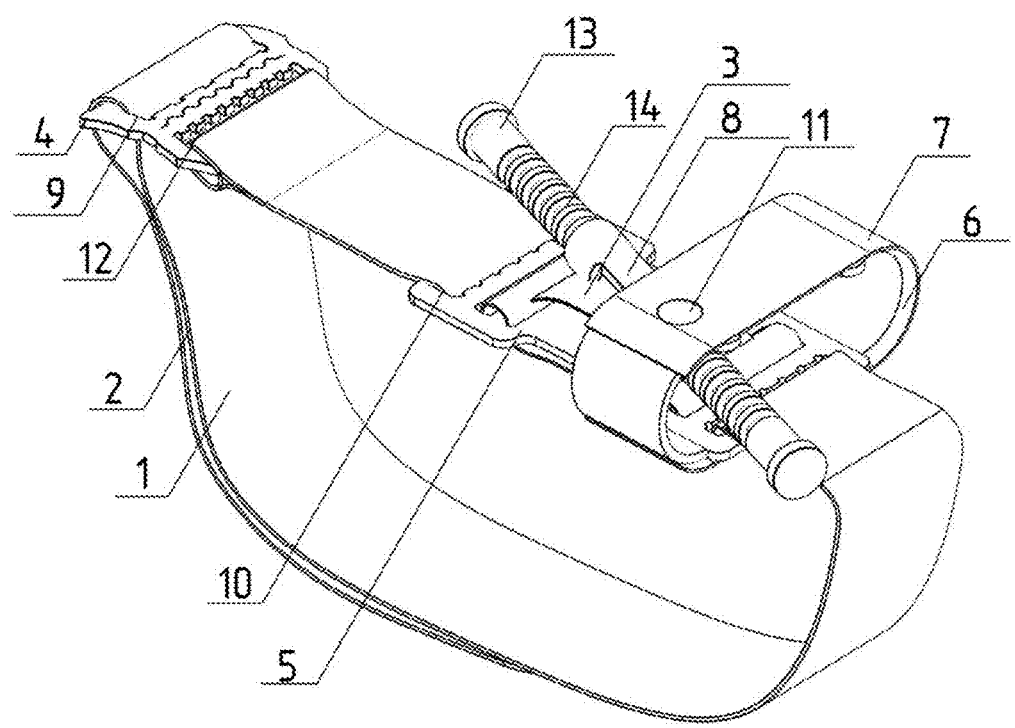
FIG. 5 depicts the styptic harness tourniquet ready for use.

In the drawing of FIG. 1 shows the general view of the styptic harness tourniquet, FIG. 2 shows the general view of the buckle, FIG. 3 shows the general view of the base, FIG. 4 shows the general view of the windlass rod, FIG. 5 shows a styptic harness tourniquet ready for use.

Styptic harness tourniquet (example) containing a casing 1 with a Velcro® fastener 2, in which a sling 3 is located. At the end of the casing 1, there is a buckle 4 and a base 5, on which the fixator 6 and the strap 7 of the fixator 6 are located. A windlass rod 8 is attached to the sling 3. Buckle 4 contains two holes 9 (example). The base 5 contains six holes 10. The strap 7 of the fixator 6 contains at least one hole 11. The holes 9 of the buckle 4 and the holes 10 of the base 5 on at least one side contain teeth 12 that have a rectangular or rounded shape (example). The windlass rod 8 at the edges contains at least 1 cm of smooth surface 13 and at least 1.5 cm of ribbed surface 14.

Styptic harness tourniquet is used by next procedure. On the wounded limb (not shown in the drawing), a casing 1 with a Velcro® fastener 2 is folded perpendicular to the limb, the end of which is threaded through two holes 9 (example) of the 30 buckle 4 and strongly tightened. After that, with the help of the windlass rod 8, by rotating it, tighten the sling 3, which is located in the casing 1. After tightening the sling 3 in order to compress the artery and stop the bleeding, the windlass rod 8 is placed in the fixator 6, which is located at the base 5. After placing windlass rod in the fixator 6, the fixator 6 is covered with the end of the casing 1 and fixed with the strap 7 of the fixator 6 with a hole 11, which provides at least 1 cm of a smooth surface 13 and at least 1.5 cm of a ribbed surface 14. The base 5 contains at least 5 six holes 10, through which a casing 1 passes with a Velcro® fastener 2 (hybrid or loop/hook that are preceding) in such a way as to allow it to pass under the base 5 avoiding the contact of the base 5 with the human body (not shown in the drawing) and with the sling 3, which is left on the surface of the base 5. Holes 9 of the buckle 4 and holes 10 of the base 5 at least on one side contain teeth 12, which have a rectangular or rounded shape (example), which provides a tighter and more reliable fixation of the case 1 with Velcro® fastener 2.

Modern hemostatic tourniquets are widely used in the medical field. Therefore, their development and improvement is an urgent task.

Existing constructive solutions of hemostatic tourniquets have a number of disadvantages, the main of which are low reliability and low efficiency of operation. So, for example, the CAT hemostatic tourniquet (Access mode www.combattourniquet.com), which was chosen as a prototype, has low reliability and operational efficiency due to too thin and soft casing and when used (twisting windless rod) causes painful feeling when applied, the lower strap of the casing is located on the surface of the base, which in some cases can lead to winding under the windless rod together with the sling of the lower strap of the casing and lead to self-blocking, which leads to incomplete blocking of blood flow, the casing with Velcro® fastener is too soft, which does not provide a stable loop when applying and can interfere in self-help. The buckle, the windless rod and the base are made of plastic, which has low operational qualities. The buckle and base holes have a small number of holes. The lower strap of the casing is located on top of the base, which does not allow it to avoid contact with the human body. In addition, the buckle and base holes do not provide a tight fit on the limb, thus not providing reliable hemostasis.

The developed styptic harness tourniquet allows eliminating imperfections and significantly increasing the reliability and efficiency of operation thanks to the introduced structural elements and connections. This is due to the introduction of 5 additional holes with teeth of different shapes into the structure of the base, which ensures more reliable contact during tightening and excludes contact of the base with the human body. The use of a windless rod which is made of aluminum or aluminum alloys allows avoiding its breaking during operation. A non-woven material is pasted on the upper part of the base, which allows avoiding rapid unwinding of the windlass rod in case if it falls out of a hand. The casing has at least two layers, which adds more rigidity and helps to form a stable loop when self-applying. In addition, the presence of a hole on the strap of the fixator allows to easily and reliably fixing the windlass rod in the fixator and can be easily fond to close the hole in the fixator, after applying the tourniquet.

The styptic harness tourniquet has experimental samples that have been tested by volunteers and received favorable reviews.

What I claimed is:

1. Styptic harness tourniquet that comprises of a casing with a hook and loop fastener, in which a sling is located, wherein at one end of the casing there is a buckle and a base on which a fixator is located, wherein the buckle contains at least one hole, wherein a windlass rod is attached to the sling, characterized in that the casing has at least two layers, the base contains at least six holes, a strap of the fixator is located on the base, the strap containing at least one hole, wherein holes of the buckle and the base have teeth on at least one side.

2. Styptic harness tourniquet according to claim 1, which characterized in that plastic is used as a material of the base and the fixator.

3. Styptic harness tourniquet according to claim 1, which characterized in that aluminum, aluminum alloys, or plastic are used as materials for the windlass rod and the buckle.

4. Styptic harness tourniquet according to claim 1, which characterized in that the teeth of the holes can have a rectangular, rounded, trapezoidal, or square shape.

5. Styptic harness tourniquet according to claim 1, characterized in that the windlass rod contains at least 1 cm of a smooth surface and at least 1.5 cm of a ribbed surface at edges of the windlass rod.

* * * * *